United States Patent [19]

Romanet et al.

[11] Patent Number: 5,183,728

[45] Date of Patent: Feb. 2, 1993

[54] PHOTOGRAPHIC SILVER HALIDE MATERIALS AND PROCESS COMPRISING NEW PYRAZOLOAZOLE COUPLERS

[75] Inventors: Robert F. Romanet; Teh-Hsuan Chen, both of Rochester, N.Y.

[73] Assignee: Eastman Kodak Company, Rochester, N.Y.

[21] Appl. No.: 580,978

[22] Filed: Sep. 12, 1990

Related U.S. Application Data

[63] Continuation of Ser. No. 297,459, Jan. 13, 1989, abandoned, which is a continuation of Ser. No. 23,518, Mar. 9, 1987, abandoned.

[51] Int. Cl.$^5$ ................................................ G03C 7/32
[52] U.S. Cl. .................................. 430/386; 430/387; 430/505; 430/558
[58] Field of Search ................ 430/558, 505, 387, 386

[56] References Cited

U.S. PATENT DOCUMENTS

| | | | |
|---|---|---|---|
| 4,443,536 | 4/1984 | Lestina | 430/532 |
| 4,540,654 | 9/1985 | Sato et al. | 430/381 |
| 4,559,297 | 12/1985 | Seto et al. | 430/551 |
| 4,639,413 | 1/1987 | Kawagishi et al. | 430/546 |
| 4,659,652 | 4/1987 | Kawagishi et al. | 430/558 |
| 4,755,455 | 7/1988 | Iwasa | 430/558 |
| 5,066,575 | 11/1991 | Sato et al. | 430/558 |

FOREIGN PATENT DOCUMENTS

| | | |
|---|---|---|
| 0178794 | 4/1986 | European Pat. Off. . |
| 0183445 | 4/1986 | European Pat. Off. . |
| 0182617 | 5/1986 | European Pat. Off. . |
| 0176804 | 9/1986 | European Pat. Off. . |
| 1247493 | 9/1971 | United Kingdom . |
| 1252418 | 11/1971 | United Kingdom . |
| 1398979 | 6/1975 | United Kingdom . |

OTHER PUBLICATIONS

Research Disclosure No. 12443, *Research Disclosure*, vol. 124, 1974, Kenneth Mason Publications Ltd., Hampshire, England.

Research Disclosure No. 17643, *Research Disclosure*, vol. 176, 1978, Kenneth Mason Publications Ltd., Hampshire, England.

*Primary Examiner*—Charles L. Bowers, Jr.
*Assistant Examiner*—Janet C. Baxter
*Attorney, Agent, or Firm*—Arthur E. Kluegel

[57] ABSTRACT

Novel pyrazoloazole dye-forming couplers contain on the azole ring a group containing a carbon atom bonded directly to the azole ring and wherein this carbon atom is bonded directly to a nitrogen atom in the group. Such couplers provide advantageous bathochromic hue shift in dyes formed from the couplers. These couplers are useful in photographic silver halide materials and processes.

17 Claims, No Drawings

PHOTOGRAPHIC SILVER HALIDE MATERIALS AND PROCESS COMPRISING NEW PYRAZOLOAZOLE COUPLERS

This is a continuation of application Ser. No. 297,459, filed Jan. 13, 1989, now abandoned, which is a continuation of Ser. No. 23,518, filed Mar. 9, 1987, now abandoned.

This invention relates to novel pyrazoloazoles as dye-forming couplers and to photographic silver halide elements and processes using such couplers.

Color images are customarily obtained in the photographic art by reaction between the oxidation product of a silver halide color developing agent and a dye-forming coupler. Pyrazolone couplers are useful for forming magenta dye images, however, pyrazoloazole couplers represent another class of couplers that are useful for this purpose. Examples of pyrazolotriazole couplers, particularly 1H-pyrazolo [3,2-c]-s-triazole couplers, are described in, for example, U.S. Pat. No. 4,443,536; U.K. Patents 1,247,493; 1,252,418 and 1,398,979. An example of such a coupler is represented by the formula:

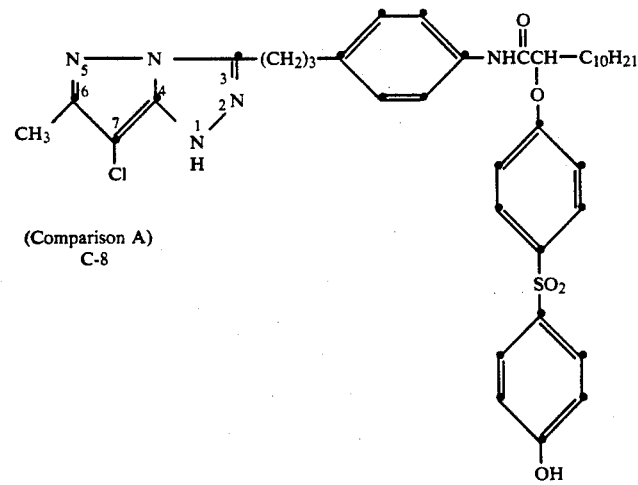

(Comparison A)
C-8

While such couplers are useful in photographic silver halide materials and processes, many such couplers have not had the desired degree of dispersibility and photographic activity to provide increased maximum dye density. Additionally, they do not always provide dyes of the desired hue.

It has been desirable to provide pyrazoloazole couplers that enable the desired bathochromic hue shift without undesired reduction in photographic activity and dispersibility.

It has been found that the described advantages are provided by a photographic pyrazoloazole coupler having substituted on the azole ring of the coupler a group represented by the structure:

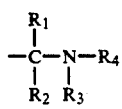

wherein $R_1$ and $R_2$ are individually hydrogen, unsubstituted alkyl, such as alkyl containing 1 to 40 carbon atoms, for example methyl, ethyl, propyl, butyl, pentyl and eicosyl; substituted alkyl, such as substituted alkyl containing 1 to 40 carbon atoms, for example alkyl substituted with a water solubilizing group, such as carboxy or hydroxy; unsubstituted aryl, such as aryl containing 6 to 40 carbon atoms, for example phenyl or naphthyl, or substituted aryl, such as substituted aryl containing 7 to 40 carbon atoms, for example, methoxyphenyl or xylyl; and other substituents that do not adversely affect the coupler;

$R_3$ and $R_4$ are individually hydrogen, unsubstituted alkyl, such as alkyl containing 1 to 40 carbon atoms, for example, methyl, ethyl, propyl, butyl, pentyl, decyl, and eicosyl; substituted alkyl, such as substituted alkyl containing 1 to 40 carbon atoms, for example,

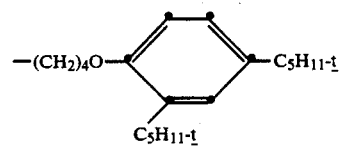

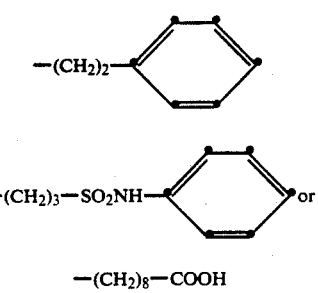

unsubstituted aryl, such as aryl containing 6 to 40 carbon atoms, for example, phenyl and naphthyl; or substituted aryl, such as substituted aryl containing 7 to 40 carbon atoms, for example, carboxyphenyl,

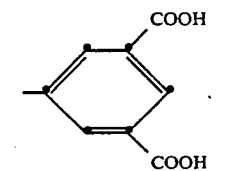

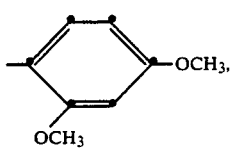

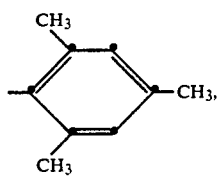

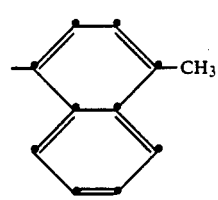

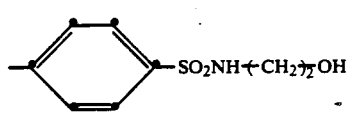

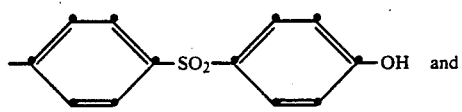

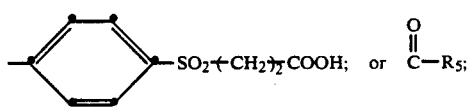

wherein at least one of $R_3$ and $R_4$ is unsubstituted or substituted alkyl, aryl or $$\overset{O}{\underset{}{\overset{\|}{C}}}-R_5;$$

wherein $R_5$ is alkyl, such as alkyl containing 1 to 40 carbon atoms, for example, unsubstituted alkyl, such as methyl, ethyl, propyl, butyl, octyl, and eicosyl or substituted alkyl, such as substituted alkyl containing 2 to 40 carbon atoms, for example,

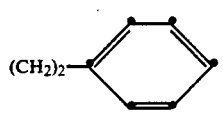

-continued

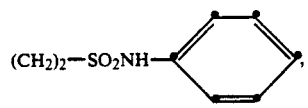

$(CH_2)_2COOH$, $(CH_2)_3COOH$, and

wherein $R_6$ is a substituent that does not adversely affect the coupler, such as alkyl, for example, alkyl containing 1 to 40 carbon atoms, such as unsubstituted or substituted alkyl, for example, methyl, ethyl, propyl, butyl, octadecyl,

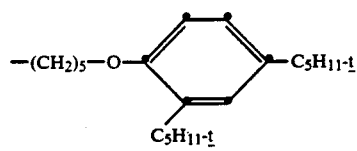

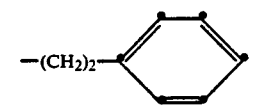

$-(CH_2)_3OH$ and $-(CH_2)_3COOH$;

unsubstituted or substituted aryl, such as aryl containing 6 to 40 carbon atoms, for example, phenyl, naphthyl, carboxyphenyl, hydroxyphenyl,

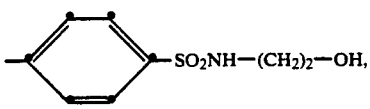

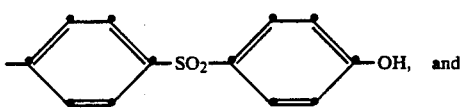

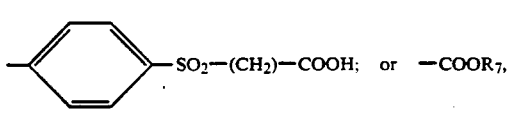

wherein $R_7$ is unsubstituted or substituted alkyl, such as ethyl, propyl, octyl, or eicosyl; or unsubstituted or substituted aryl, such as phenyl, naphthyl, carboxyphenyl or xylyl. The above group containing $R_1$, $R_2$, $R_3$ and $R_4$ preferably comprises a ballast group.

These pyrazoloazole couplers not only provide a desired bathochromic shift in hue and enable increased maximum dye density but also enable formation of improved dispersions without adverse effects on desired properties, such as sensitivity of the photographic material.

The pyrazoloazole couplers are typically pyrazolotriazoles or pyrazolodiazoles; however, other pyrazoloazole couplers are also useful. Combinations of pyrazoloazole couplers according to the invention are also useful.

Particularly useful pyrazolotriazoles are pyrazolo [3,2-c]-s-triazoles and pyrazolo [2,3-b]-s-triazoles. The pyrazolo [2,3-b]-s-triazole can also be named as a pyrazolo [1,5-b]-1,2,4-triazole.

A pyrazoloazole coupler according to the invention is represented by the formula:

wherein A is a pyrazoloazole coupler nucleus and, $R_1$, $R_2$, $R_3$ and $R_4$ are as described.

A typical pyrazolotriazole coupler according to the invention is represented by the structure:

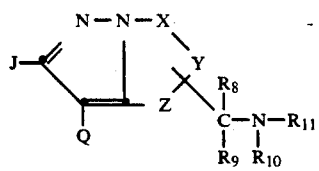

wherein:
J is a substituent which does not adversely affect the desired properties of the coupler; particularly unsubstituted or substituted alkyl or unsubstituted or substituted aryl;

Q is hydrogen or a coupling-off group such as halogen or a coupling-off group known to be useful for 2-equivalent couplers in the photographic art;

X, Y and Z are individually selected from carbon and nitrogen atoms necessary to complete an azole ring, particularly a triazole ring with unsaturated bonding being present in the ring as needed;

$R_8$ and $R_9$ are individually hydrogen or unsubstituted or substituted alkyl; or unsubstituted or substituted aryl, as defined for $R_1$ and $R_2$;

$R_{10}$ and $R_{11}$ are individually hydrogen, unsubstituted or substituted alkyl; unsubstituted or substituted aryl or

as defined for $R_3$ and $R_4$; wherein at least one of $R_{10}$ and $R_{11}$ is alkyl, aryl or

$R_{12}$ is unsubstituted or substituted alkyl, unsubstituted or substituted aryl or NH—$R_{13}$; and $R_{13}$ is unsubstituted or substituted alkyl or unsubstituted or substituted aryl.

Preferred 1H-pyrazolo[3,2-c]-s-triazole couplers are represented by the formula

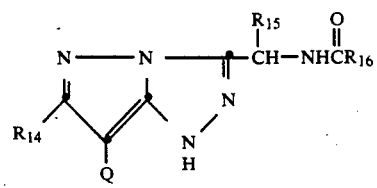

wherein:
$R_{14}$ is a substituent that does not adversely affect the desired properties of the pyrazolotriazole coupler particularly unsubstituted or substituted alkyl or unsubstituted or substituted aryl;

$R_{15}$ is unsubstituted or substituted alkyl;

$R_{16}$ is unsubstituted or substituted alkyl or NH—$R_{17}$;

$R_{17}$ is unsubstituted or substituted alkyl, or unsubstituted or substituted aryl; and Q is hydrogen or a coupling-off group.

Illustrative examples of the group

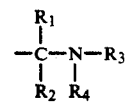

are:

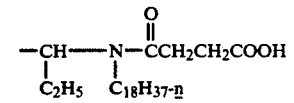

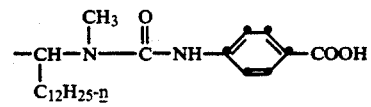

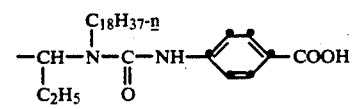

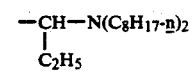

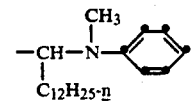

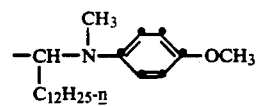

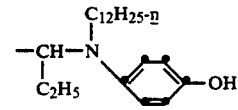

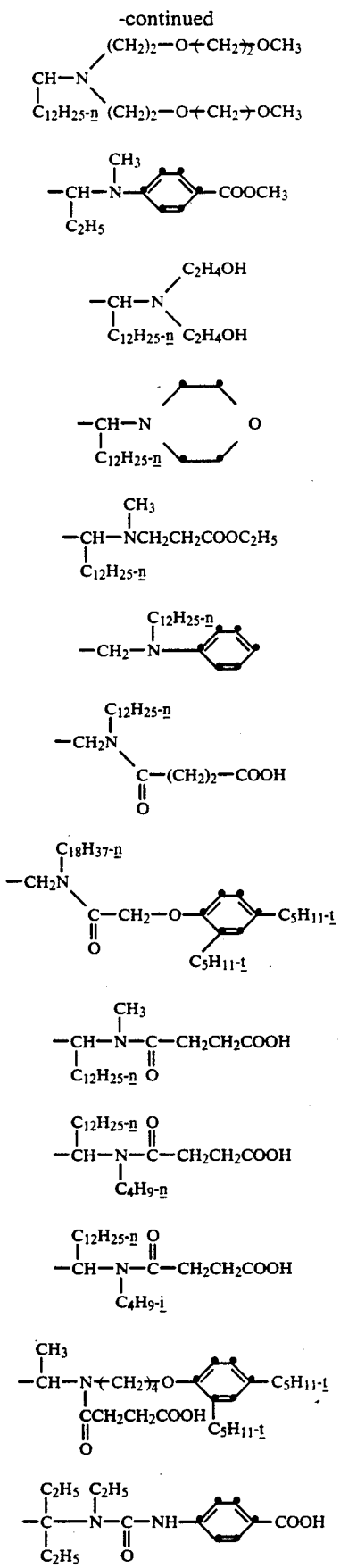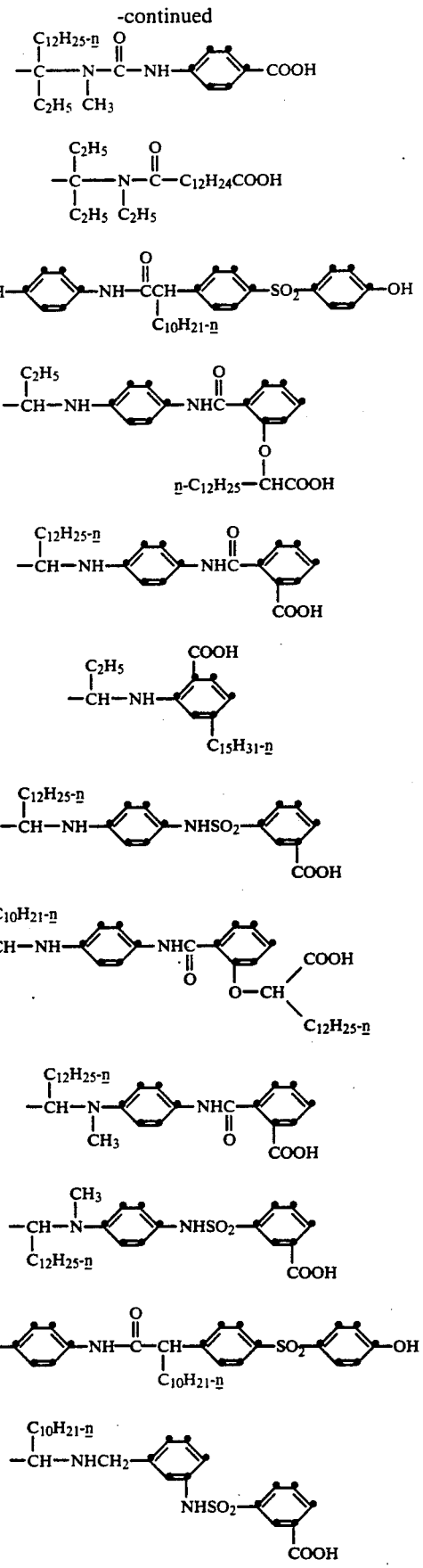

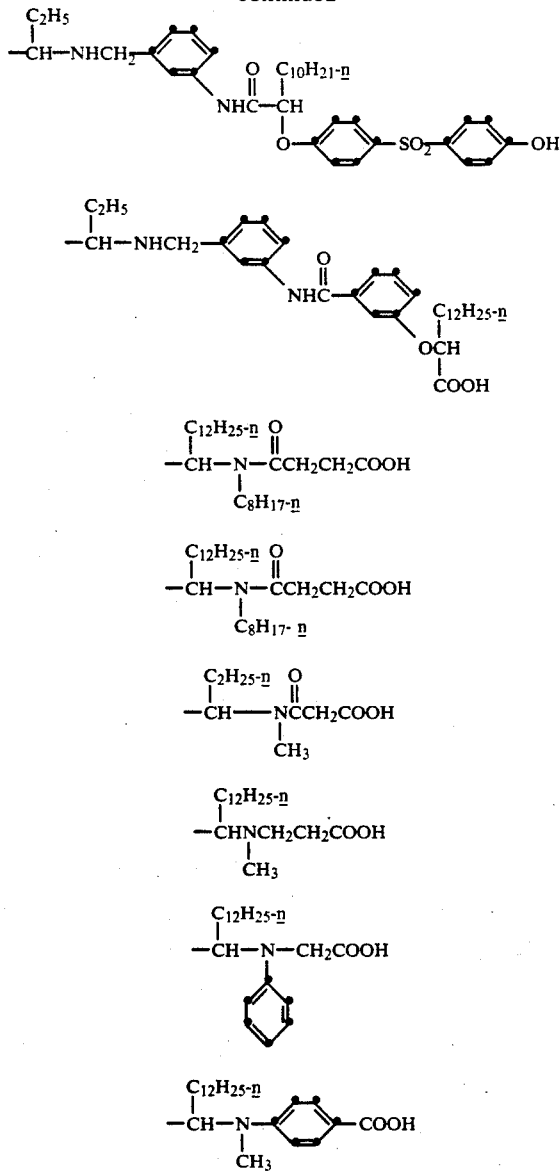

Particularly useful pyrazoloazole couplers are 1H-pyrazolo[3,2-c]-s-triazole couplers, according to the invention, and contain the group

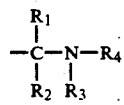

as described in the 3-position. Such couplers preferably contain in the 6-position an aryl group, particularly a phenyl or naphthyl group, which can be unsubstituted or optionally substituted, or an alkyl unsubstituted or substituted group, such as alkyl containing 1 to 40 carbon atoms.

A pyrazoloazole coupler, particularly a pyrazolotriazole coupler, typically contains a group which can aid solubility or diffusion resistance and produces a dye hue of desired hue upon reaction of the coupler with an oxidized color developing agent. For example, 1H-pyrazolo[3,2-c]-s-triazole couplers, according to the invention typically contain such a group in the 6-position.

A pyrazolotriazole coupler, for example, typically contains on the pyrazolotriazole nucleus, for instance in the 6-position of a 1H-pyrazolo[3,2-c]-s-triazole, a substituent that does not adversely affect the coupler, such as one of the following groups: alkyl, such as alkyl containing 1 to 30 carbon atoms, for example, methyl, ethyl, propyl, n-butyl, t-butyl, octyl and eicosyl; aryl, such as aryl containing 6 to 30 carbon atoms, for example, phenyl, naphthyl and mesityl. Such groups also include amino; acylamino, such as acylamino containing 2 to 30 carbon atoms, for example, acetamido, benzamido and stearamido; ureido; carboxy; alkanesulfonyl, such as ethanesulfonyl and butanesulfonyl; cyano (—CN); carbamyl, such as methyl carbamyl and hexyl carbamyl; sulfamyl, such as dioctyl sulfamyl and methyloctadecyl sulfamyl; sulfonamido; carboxamido; cycloalkyl, such as cyclohexyl and cyclopentyl; alkoxy, such as alkoxy containing 1 to 30 carbon atoms, for example, methoxy, i-butoxy and dodecyloxy; alkoxycarbonyl, such as ethoxycarbonyl and dodecyloxycarbonyl; aryloxycarbonyl, such as phenoxycarbonyl; alkylthio, such as alkylthio containing 1 to 30 carbon atoms, for example, methylthio and i-butylthio; aryloxy, such as aryloxy containing 6 to 30 carbon atoms, for example, phenoxy and naphthoxy; arylthio, such as arylthio containing 6 to 30 carbon atoms, for example, phenylthio; and heterocyclic groups, such as comprised of atoms selected from the group consisting of carbon, oxygen, nitrogen and sulfur atoms necessary to complete a 5- or 6-member heterocyclic ring, such as pyridyl, benzoxazolyl, furyl and thienyl. These groups on the pyrazolotriazole coupler are unsubstituted or optionally substituted with groups that do not adversely affect the desired properties of the pyrazolotriazole coupler. Examples of useful substituents can include ballast groups and coupler moieties known to be useful in the photographic art, or alkyl, such as alkyl containing 1 to 4 carbon atoms, for example, methyl, ethyl and t-butyl.

An example of such a group that is useful in the 6-position of a 1H-pyrazolo[3,2-c]-s-triazole coupler is a tertiary carbon group:

wherein:

$R_{18}$, $R_{19}$ and $R_{20}$ are individually substituents that do not adversely affect the coupler, such as halogen, for example, chlorine, bromine and fluorine; alkyl, such as alkyl containing 1 to 30 carbon atoms, for example, methyl, ethyl, propyl, butyl, pentyl, ethylhexyl and eicosyl; cycloalkyl, such as cyclohexyl and cyclopentyl; alkoxy, such as alkoxy containing 1 to 30 carbon atoms, for example, methoxy, ethoxy, butoxy and dodecyloxy; carboxy; amino, such as dioctylamino, dimethylamino and dodecylamino; carbonamido, such as acylamino containing 1 to 30 carbon atoms, for example, acetamido, stearamido, ureido and benzamido; alkylthio, such as alkylthio containing 1 to 30 carbon atoms, for example, methylthio, ethylthio, propylthio and dodecylthio; aryl, such as aryl containing 6 to 30 carbon atoms, for example, phenyl, naphthyl and mesityl; aryloxy, such as aryloxy containing 6 to 30 carbon atoms, for example, phenoxy and naphthoxy; cyano; nitro; sulfonamido; sulfamyl; carboxamido; alkylthio, such as ethylthio and butylthio; arylthio, such as arylthio containing 6 to 30 carbon atoms, for example, phenylthio and naphthylthio; or a heterocyclic group, such as a heterocyclic group comprised of atoms selected from carbon, oxygen, nitrogen and sulfur atoms necessary to complete a 5- or 6-member ring, for example, pyrrolyl, oxazolyl and pyridyl. Optionally, in such a tertiary group, $R_{18}$ can form with one of $R_{19}$ and $R_{20}$ a heterocyclic ring, such as a heterocyclic ring comprised of atoms selected from carbon, nitrogen, oxygen and sulfur atoms necessary to complete a 5- or 6-member heterocyclic ring, for example, oxazole, pyridine, pyrrole and thiophene; or, $R_{18}$ can form with one of $R_{19}$ and $R_{20}$ a carbocyclic ring, such as cyclohexyl or norbornyl; or $R_{18}$, $R_{19}$ and $R_{20}$ can comprise the carbon and hydrogen atoms necessary to complete a ring, such as an adamantyl ring.

The groups $R_{18}$, $R_{19}$ and $R_{20}$ are unsubstituted or optionally substituted with groups that do not adversely affect the desired properties of the pyrazolotriazole coupler. The groups can be optionally substituted with, for example, alkyl, such as alkyl containing 1 to 20 carbon atoms, for example, methyl, ethyl, propyl and butyl; aryl, such as phenyl and naphthyl; or phenolic, carboxylic acid and heterocyclic substituent groups. Substituents can include ballast groups and coupler moieties which are known to be useful in the photographic art.

Examples of useful tertiary carbon groups are

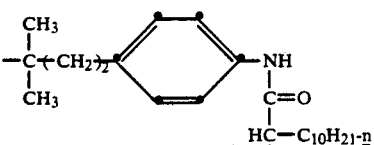

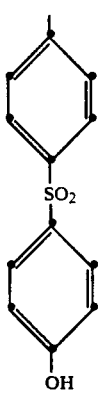

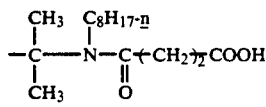

-continued

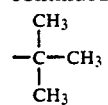

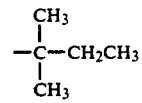

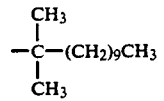

The pyrazoloazole couplers contain in the coupling position, that is the 7-position in a 1H-pyrazolo[3,2-c]-s-triazole coupler, hydrogen or a coupling-off group, also known as a leaving group.

Coupling-off groups, defined by Q herein, are well known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development accelerations, bleach inhibition, bleach acceleration, color correction and the like. Representative classes of coupling-off groups include halogen, particularly chlorine, bromine and fluorine, alkoxy, carbonamido, imido, aryloxy, particularly substituted phenoxy, heterocycloxy, sulfonyloxy, acyloxy, heterocyclyl, thiocyano, alkylthio, arylthio, particularly substituted phenylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766; and in U.K. patents and published application numbers 1,466,728; 1,531,927; 1,533,039; 2,006,755A and 2,017,704A; the disclosures of which are incorporated herein by reference.

Examples of specific coupling-off groups are

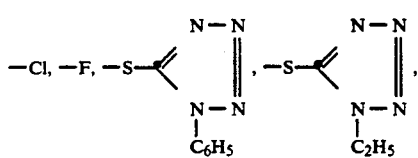

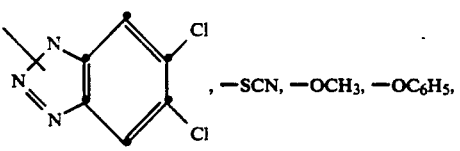

—OCH$_2$CONHCH$_2$CH$_2$OH, —OCH$_2$CONHCH$_2$CH$_2$OCH$_3$,

—OCH$_2$CONHCH$_2$CH$_2$OCOCH$_3$,

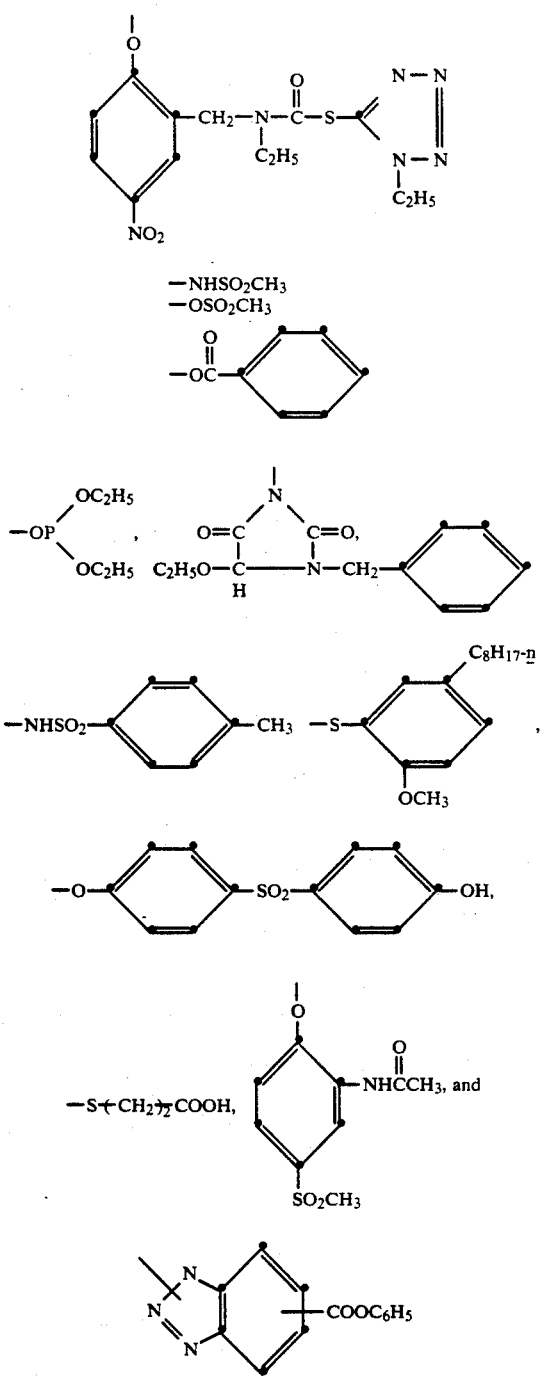

A ballast group as described is an organic radical of such size and configuration as to confer on the coupler molecule sufficient bulk to render the coupler substantially non-diffusible from the layer in which it is coated in a photographic element. Couplers of the invention can contain ballast groups, or be bonded to polymeric chains through one or more of the groups described herein. For example, one or more coupler moieties can be attached to the same ballast group. Representative ballast groups include substituted or unsubstituted alkyl or aryl groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfoxide, arylsulfoxide, alkanesulfonyl, arenesulfonyl, amino, anilino, sulfonamido and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkanesulfonyl, arenesulfonyl, sulfonamido and sulfamoyl substituents containing 1 to 30 carbon atoms and 6 to 30 carbon atoms, respectively, and can be further substituted with such substituents.

Pyrazoloazole couplers according to the invention are prepared by the general method of synthesis described in *Research Disclosure*, August 1974, Item No. 12443 published by Kenneth Mason Publications, Ltd., The Old Harbourmaster's, 8 North Street, Emsworth, Hampshire PO10 7DD, England and U.S. Pat. No. 4,540,654. An illustrative synthesis scheme I is as follows:

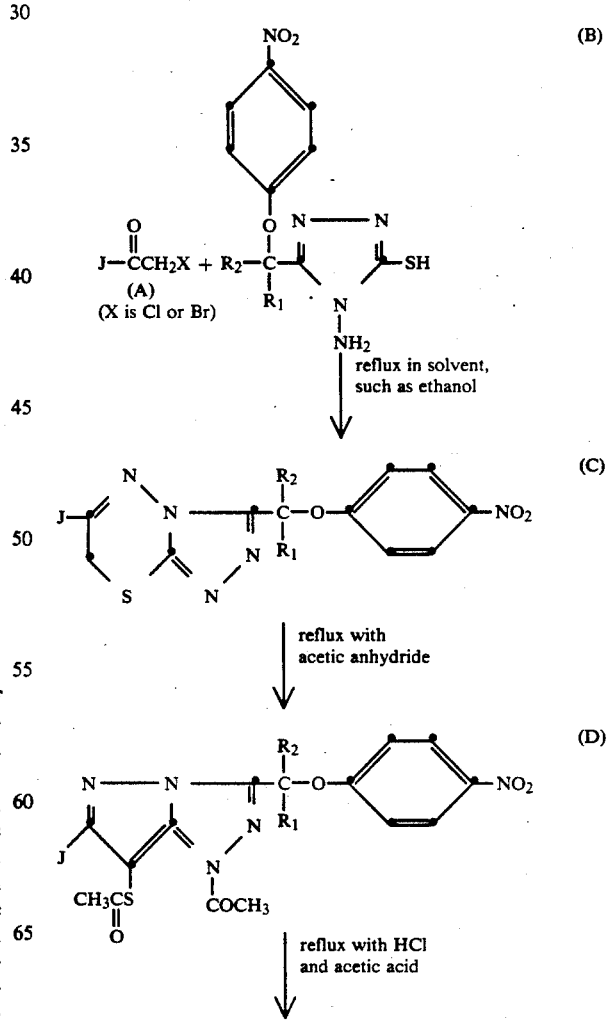

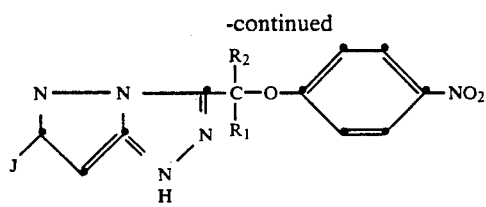 (E)

(remove elemental sulfur formed)
(add optional coupling-off group, such as chlorine by reaction with N-chlorosuccinimide)

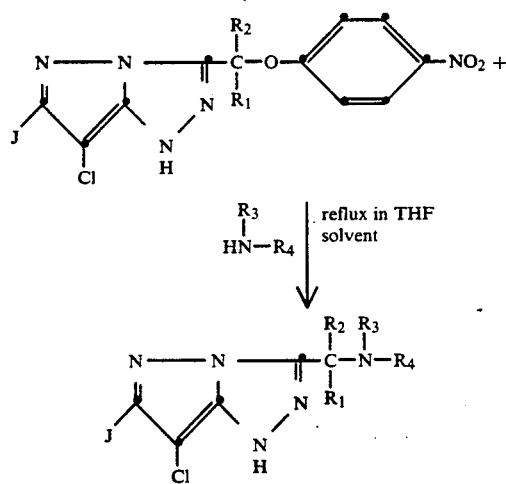

wherein $R_1$, $R_2$, $R_3$, $R_4$ and J are as defined.

An optional method for preparing an intermediate (K) for preparing 1H-pyrazolo[3,2-c]-s-triazole couplers according to the invention is illustrated in the following method:

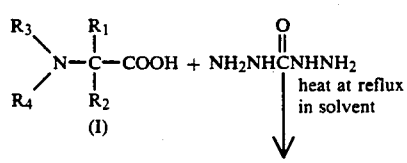 (I)

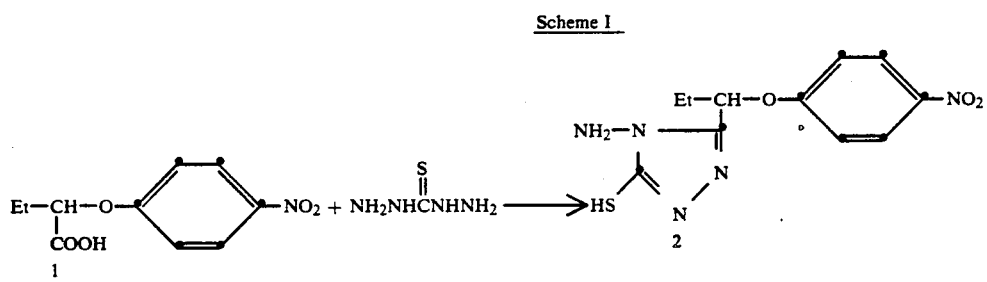 (K)

wherein $R_1$, $R_2$, $R_3$ and $R_4$ are as described.

This intermediate (K) can be useful to form pyrazolotriazole (H) without the need for formation of a p-nitrophenoxy group as in intermediate (B).

Another optional method for preparing an intermediate (K) for preparing pyrazolotriazoles according to the invention is illustrated in the following sequence:

wherein $R_1$, $R_2$, $R_3$ and $R_4$ are as described.

Illustrative examples of the preparation of pyrazoloazole couplers according to the invention are as follows:
(Et herein means —$C_2H_5$.)
($Ac_2O$ herein means acetic anhydride.)

SYNTHESIS EXAMPLE A

Scheme I

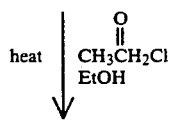

-continued
Scheme I
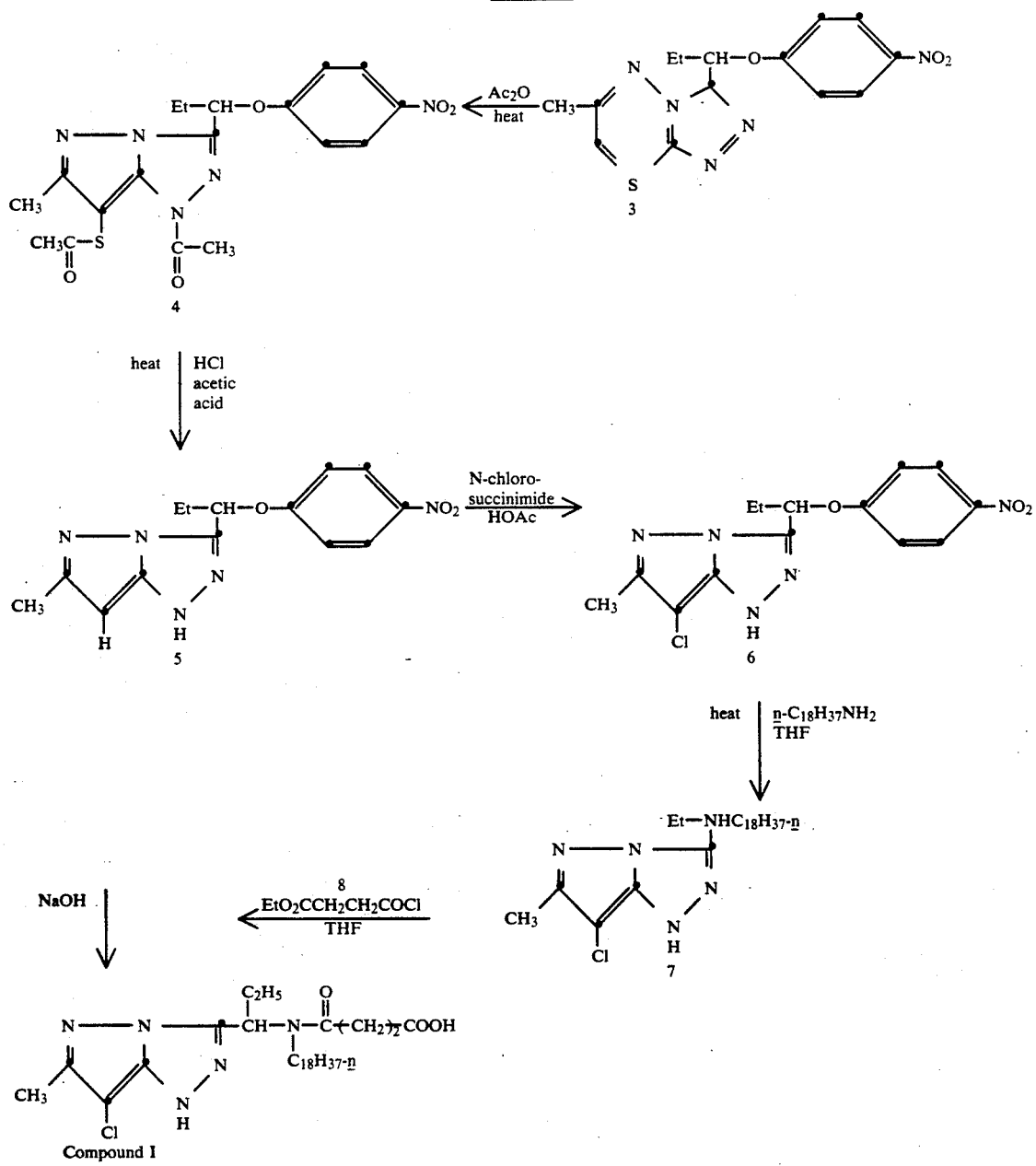
Compound I
SYNTHESIS EXAMPLE A
Preparation of Intermediate 2
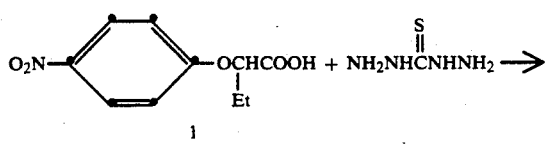
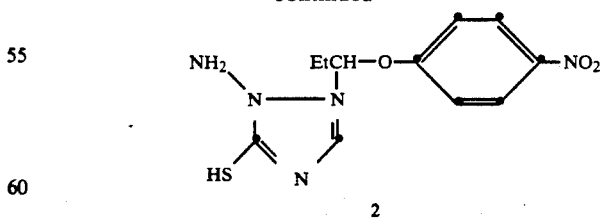
10.0 gm (0.044 mol) acid 1 and 5.2 gm (.049 mol) thiocarbohydrazide were mixed intimately and heated to 130° C. for three hours. EtOH was added to the hot mixture and the mixture allowed to cool with stirring overnight. The desired intermediate was a white solid (8.1 gm) (62%). The intermediate was filtered and air dried. (NMR and nmr herein mean nuclear magnetic resonance.)

NMR analysis: H nmr: δ1.0 (t,3H); 2.22 (q,2H); 5.6–5.9 (s,m,3H); 7.25 (d,2H); 8.25 (d,2H).

Preparation of Intermediate 3

10 grams (0.034 mol) of 2 were refluxed 3 hours with 3.6 ml (0.045 mol) chloroacetone, cooled, and impregnated on silica gel. The product was chromatographed to obtain 9.2 gm of yellow glass. This was triturated overnight with ether to give 8.2 gm (73%) light tan solid 3.

NMR Analysis: 'H NMR: δ1.1 (t,3H); 2.0–22.5 (s,q, 5H); 3.65 (s,2H), 7.68 (t,1H); 7.15 (d,2H) 8.15 (d,2H).

Preparation of Intermediate 4

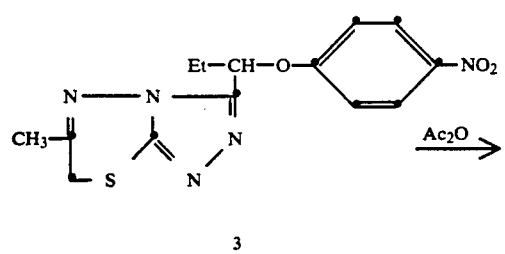

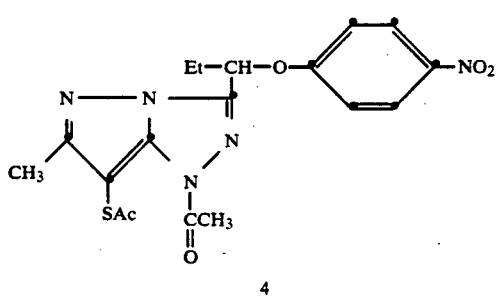

8 gm (0.024 mol) of 3 were refluxed overnight in acetic anhydride. The product was cooled and added to a mixture of water and ether and then stirred 4 hours. The organic layer washed with water, dried over magnesium sulfate, and evaporated to a brown viscous oil, 8.3 gm.

NMR Analysis: 'H NMR: δ1.2 (t,3H); 2.1–2.7 (s,s,s,m11H); 5.5(t,1H); 7.05 (d,2H) 8.05 (d,2H).

Preparation of Intermediate 5

5.0 gm of 4 was refluxed one hour with 50 ml CONC HCl and 50 ml glacial acetic acid. The product was cooled and added to water. Ethyl acetate was added and the organic layer washed, dried (M₉SO₄), and evaporated to 3.4 gm oil. The product was triturated with CH₃CN to yield 1.7 gm (47%) white solid 5.

NMR Analysis: 'H NMR: δ0.9 (t,3H); 1.0–1.8 (m,2H); 5.58 (5,1H); 5.62 (6,1H); 7.13 (d,2H); 8.16 (d,2H).

Preparation of Intermediate 6

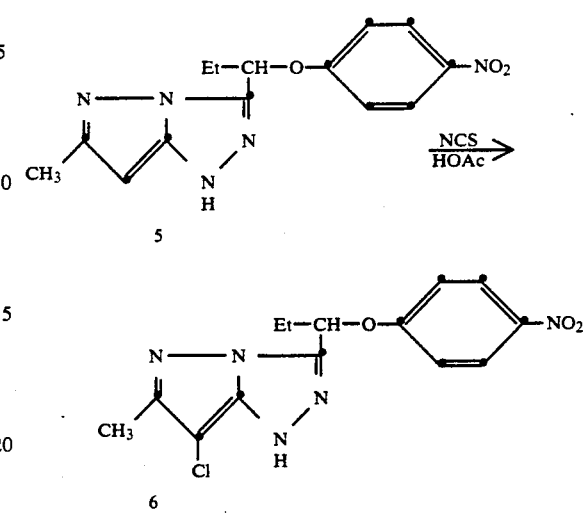

0.86 gm (0.0064 mol) N-chlorosuccinimide added to 2.0 gm (0.0066 mol) 5 dissolved in 10 ml acetic acid and stirred one hour at room temperature. The mixture added to water, ethyl acetate added and the organic layer washed with water, dried ($M_gSO_4$), and evaporated to light yellow solid, 2.1 gm (98%).

NMR Analysis: 'H NMR: δ1.05 (t,3H); 2.15–2.65 (s,m,5H); 5.55 (t,1H); 7.1 (d,2H); 8.15 (d,2H); 9.55 (s,1H).

Preparation of Intermediate 7

A mixture of 5.0 gm (0.015 mol) of 6 and 4.0 gm (0.015 mol, octadecylamine were refluxed one hour in 200 ml THF. The product was cooled and added to water. Ether was added and the organic layer washed with water, twice with saturated $Na_2CO_3$ and evaporated to 7.5 gm brown oil. The brown oil was chromatographed on silica gel to yield 4.3 gm (62%) light brown oil 7.

Analysis: Found C: 67.2; H:10.1; N 15.1. Theo C: 67.0; H: 10.4; N: 15.0.

NMR Analysis: (CDCl₃): δ0.90 (m,6H), 1.0–1.6 (m,32H), 1.98–2.7 (m,7H), 4.15 (t,1H).

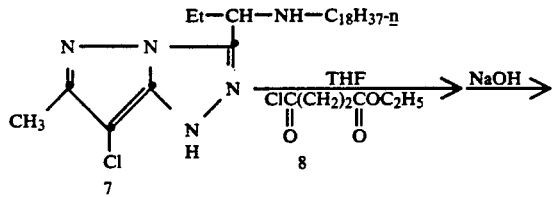

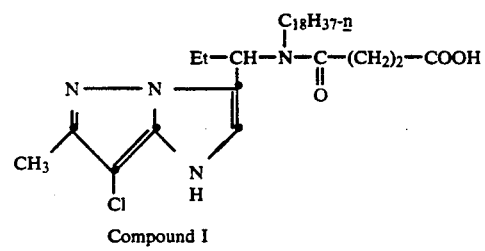

Compound I 2.1 gm (0.0045 mol) 7 was refluxed with 1.68 gm (0.0102 mol) 8 in 30 ml THF for 10 minutes. The product was added to ether and water and the organic layer washed, dried and evaporated. The residue dissolved in 20 ml THF and 20 ml methanol and 1 ml of a 50% solution of NaOH in water added. The product was stirred at ambient temperature for one half hour and then added to dilute HCl. Ether was added and the organic layer washed, dried and evaporated to dark oil. The product was chromatographed on silica gel to obtain 1.8 gm oil.

Analysis: Found: N: 11.8; C: 63.1; H: 9.6. Theo: N:12.4; C: 63.6; H: 93.

SYNTHESIS EXAMPLE B

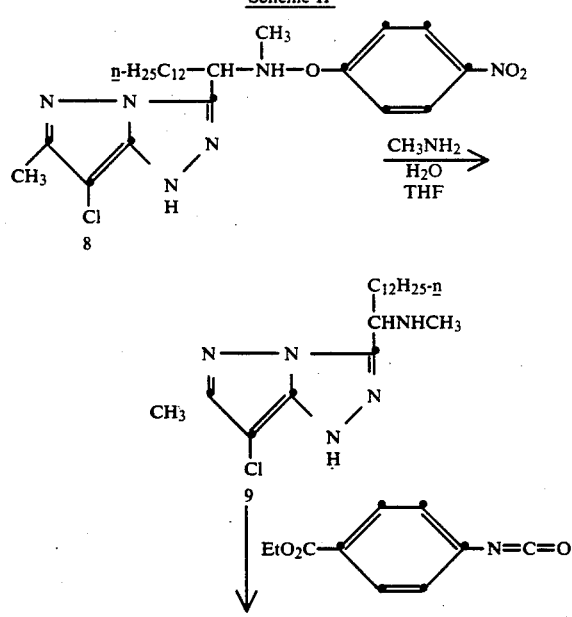

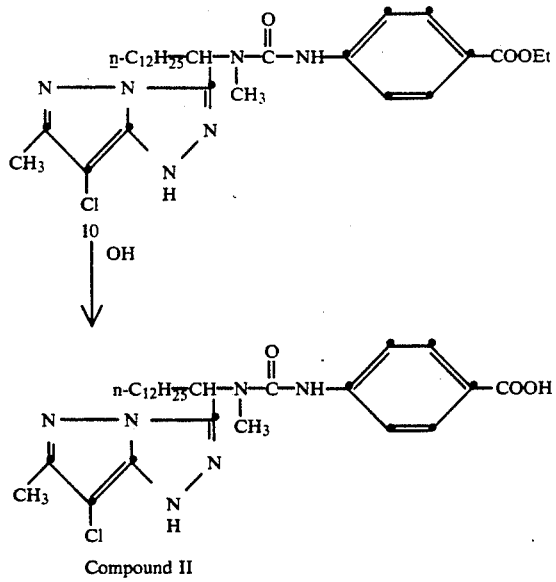

16 ml of a solution of methylamine in water, (40%), was added with stirring to 20 gm of compound 8 (obtained in the same manner as 6) and stirred at room temperature for one half hour. Water and ether were added and the organic layer washed with water, then $Na_2CO_3$ solution. Water and dried ($M_gSO_4$) and evaporated to solid. The product was triturated with ether to obtain 6.6 gm white solid 9.

5.4 gm (0.015 mol) 9 and 2.64 gm (0.015 mol) of isocyanate were refluxed in 20 ml THF for 5 minutes. After cooling, water and ethyl acetate were added. The organic layer was washed, dried, and evaporated to a tan solid. The product was triturated with acetonitrile to give 7.6 gm off-white solid 10.

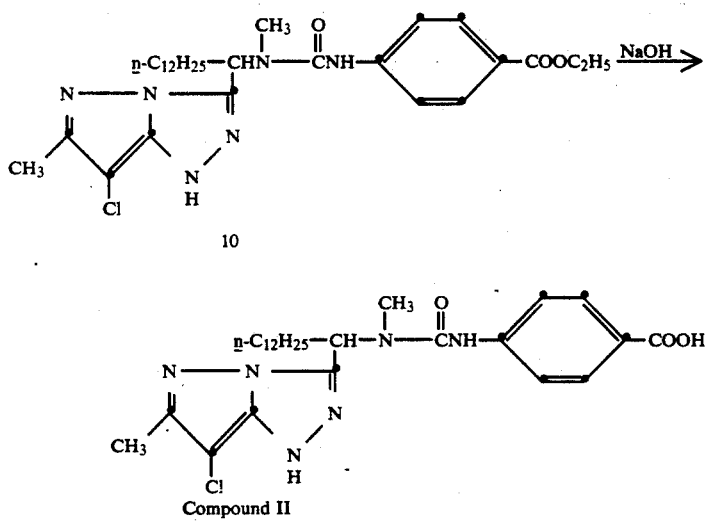

7.5 gm 10 was dissolved in 100 ml THF and 100 ml MeOH and 30 ml of a 50% solution of sodium hydroxide were added. After stirring one hour the reaction mixture was added to dilute HCl. Ethyl acetate was added and the organic layer washed, dried, and evaporated. The product was crystallized from acetonitrile to give 6.0 gm white solid. MP 178.5°–180° C.

Analysis Found: N: 15.9; C: 61.0; H: 7.5. Theoretical: N: 16.0; C: 60.2; H: 7.6.

SYNTHESIS EXAMPLE C

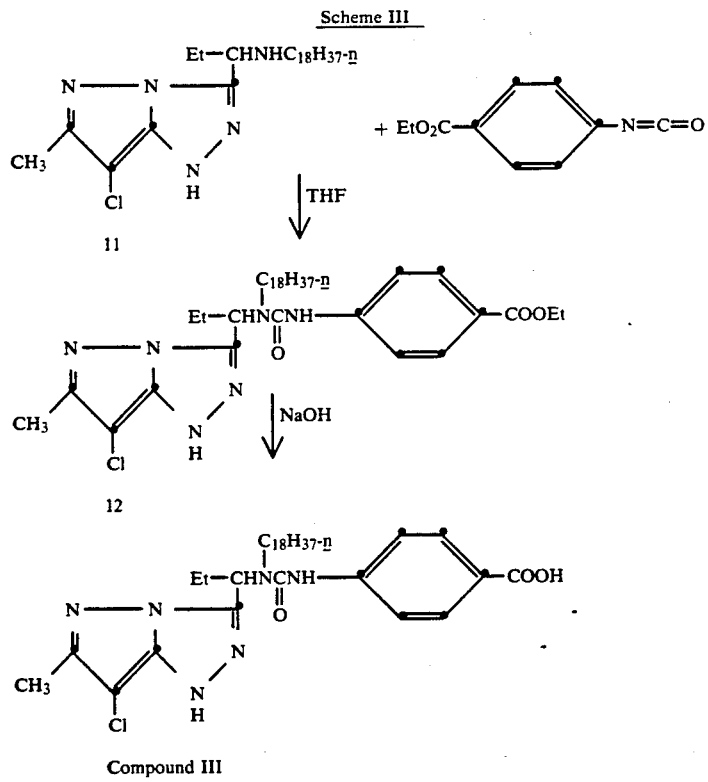

5.0 gm (0.011 mol) of 11 and 4.0 gm (0.022 mol) of the isocyanate were refluxed one half hour in 20 ml THF. The product was cooled and added to water and ethyl acetate. The organic layer was washed, dried, and evaporated and chromatographed on silica gel. The product was triturated with $CH_3CN$ to obtain 5.2 gm white solid 12.

50 grams of 12 were dissolved in a mixture of 100 ml THF and 100 ml MeOH and 20 ml of a 50% solution of NaOH in water added. After stirring at room temperature one hour the product was added to dilute HCl. Ethyl acetate was added and the organic layer washed, dried and evaporated. The solid was crystallized from acetonitrile to give 4.5 grams white solid Compound III. MP 178.5°–180.0° C.

Analysis: Found N: 13.3; C: 65.2; H: 8.7; Theoretical N: 13.4; C: 64.9; H 8.5.

SYNTHESIS EXAMPLE D

Scheme IV

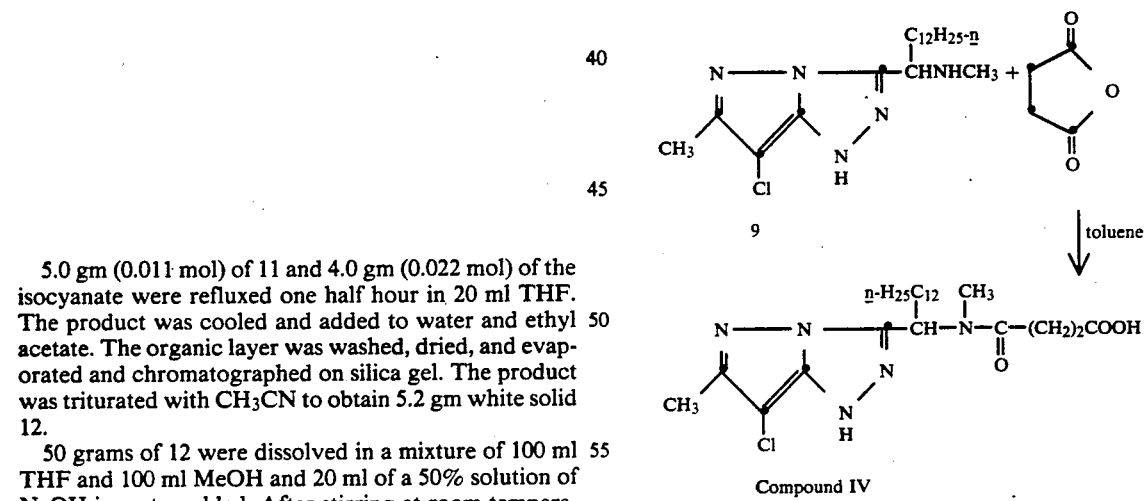

5.8 gm (0.016 mol) of 9, preparation of which is described in Scheme II was refluxed 10 minutes with 1.7 gm (0.017 mol) of succinic anhydride in 25 ml toluene and added to water. The organic layer was washed, dried and evaporated and chromatographed on silica gel. The produce was triturated with acetonitrile to yield a white solid, 3.0 gm. mp 112°–113° C.

Analysis: Found: N: 14.9; C: 59.1; H: 7.9; Theoretical: N: 15.0; C: 59.0; H 8.2.

SYNTHETIC EXAMPLE E

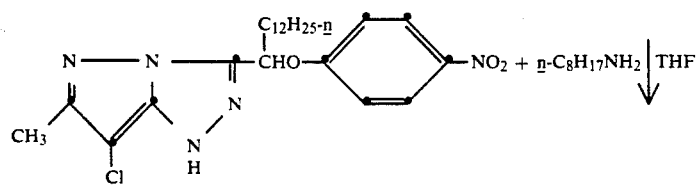

8

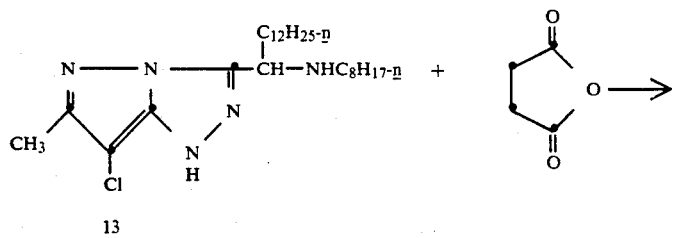

13

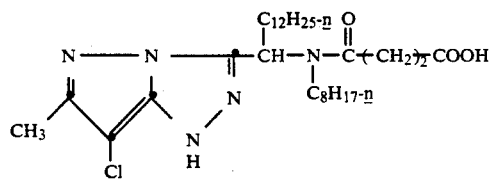

Compound V

Compound V was made from 13 in the same way as Compound IV was made from 9 (see Scheme IV). Compound 13 was made from 8 in the same way as 9 was made from 8.

NMR Analysis: H NMR: δ8.9 (t.3H); 0.9–1.6 (m,40H); 1.9–2.5 (m,s,5H); 2.6–2.9 (m,4H); 3.15–3.5 (m,2H); 5.3 and 6.0 (t,1H).

Compound 14 was prepared from 6 in the same manner as 7 was prepared from 6 and subsequently converted into Compound VI in the same fashion as 13 was converted to Compound V.

NMR Analysis: $^1$H NMR: δ0.65 (t,3H); 0.75 (t,3H); 1.3–1.5 (m,12H); 1.6–2.0 (m,8H); 2.37 (s,3H); 2.39–2.55

SYNTHETIC EXAMPLE F

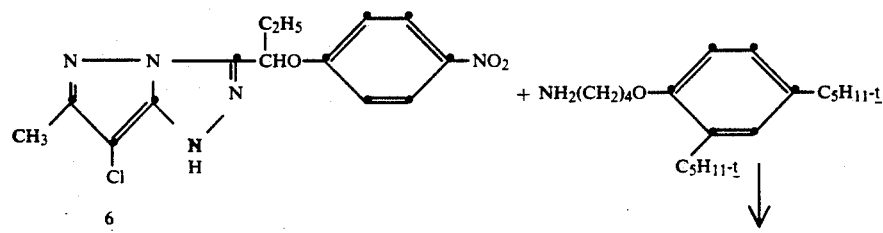

6

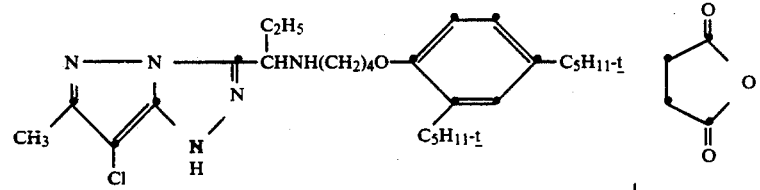

14

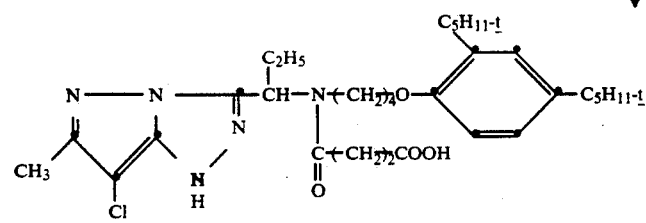

Compound VI (m,2H); 2.7-3.0 (m,4); 3.3-3.6 (m,2H); 3.85-4.0 (m,2H); 5.3+6.0 (t,t,1H); 6.83 (m,1H); 7.18 (m,1H); 7.25 (s,1H).
Analysis: Found: C: 63.9; H: 8.1; N: 11.6. Theoretical: C: 63.8; H: 8.0; N: 11.6.
SYNTHETIC EXAMPLE G
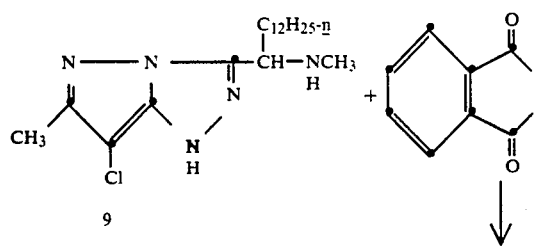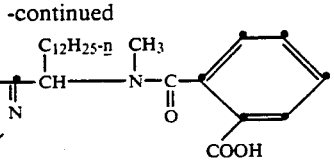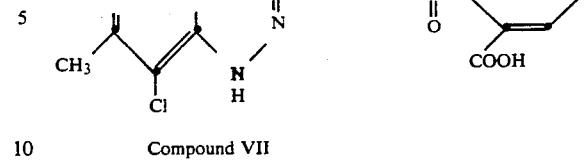
Compound VII
Compound VII was prepared from 9 in the same way as IV was prepared from 9.
Analysis: Found: C: 63.2; H: 7.5; N: 13.8. Theoretical: C: 62.8; H: 7.4; N: 13.6.
$^1$H NMR δ:0.9 (t,3H); 1.0-1.6 (m,23H); 2.0-2.4 (m,s,sh); 2.8 (s,3H); 5.0+2.6.3 (m,m,1H); 7.35-7.8 (m,3H); 8.19 (t,1H).
The following compounds were prepared in a similar manner:
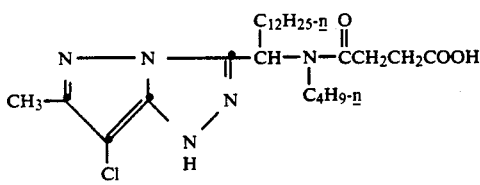
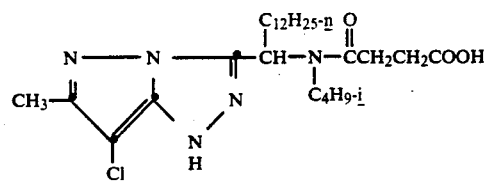
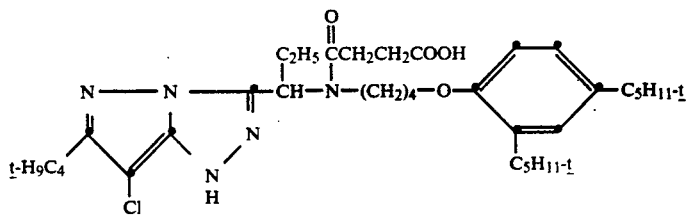
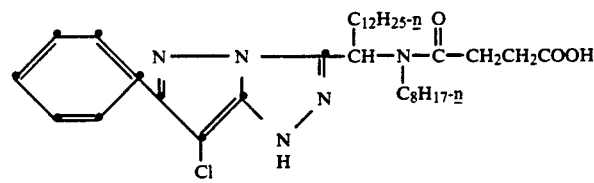
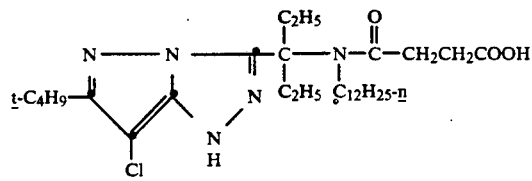
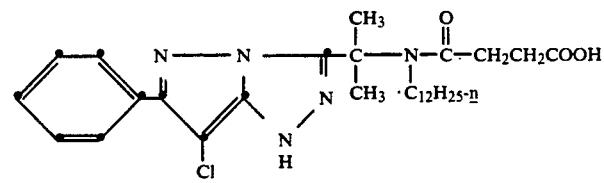

-continued

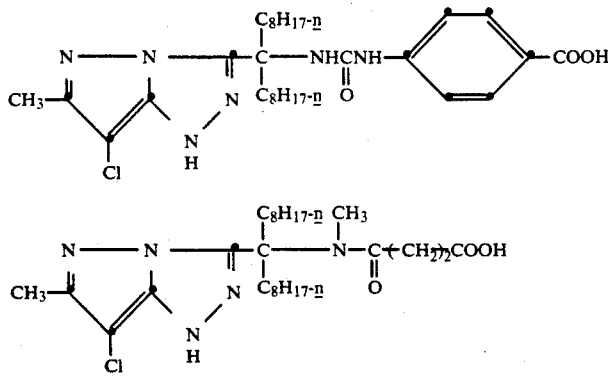

The pyrazoloazole couplers of the invention can be used for purposes and in ways in photographic materials in which pyrazoloazole couplers are known to be useful in the photographic art.

The photographic elements can be single color elements or multicolor elements. In a multicolor element, the dye-forming coupler of this invention is usually associated with a green-sensitized emulsion, although it could be associated with an unsensitized emulsion or an emulsion sensitized to a different region of the spectrum. Multicolor elements typically contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference will be made to Research Disclosure, December 1978, Item No. 17643, the disclosures of which are incorporated herein by reference. This publication will be identified hereafter by the term "Research Disclosure".

The silver halide emulsions employed in the elements of this invention can be either negative-working or positive-working. Suitable emulsions and their preparation are described in Research Disclosure Sections I and II and the publications cited therein. Suitable vehicles for the emulsion layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein.

These couplers can be incorporated in the elements and emulsion as described in Research Disclosures of Section VII, paragraph C and the publications cited therein.

The photographic elements of this invention or individual layers thereof, can contain, for example, brighteners (see Research Disclosure Section V), antifoggants and stabilizers (See Research Disclosure Section VI), antistain agents and image dye stabilizer (see Research Disclosure Section VII, paragraphs I and J), light absorbing and scattering materials) see Research Disclosure Section VIII), hardeners (see Research Disclosure Section XI), plasticizers and lubricants (see Research Disclosure Section XIII), matting agents (see Research Disclosure Section XVI) and development modifiers (see Research Disclosure Section XXI) colored masking couplers, bleach accelerators, inhibitors and competing couplers.

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride,
4-amino-3-methyl-N-ethyl-N-β-(methanesulfonamido)ethylaniline sulfate hydrate,
4-amino-3-methyl-N-ethyl-N-β-hydroxyethylaniline sulfate,
4-amino-3-β-(methanesulfonamido)ethyl-N,N-diethylaniline hydrochloride and
4-amino-N-ethyl-N-(2-methoxyethyl)-m-toluidine-di-p-toluenesulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing, and drying.

The following examples further illustrate the invention.

EXAMPLES 1-37

Photographic Elements Comprising Pyrazoloazole Couplers of the Invention

Photographic elements were prepared by coating a cellulose acetate-butyrate film support with a photosensitive layer containing a silver bromoiodide emulsion at 0.91 gm Ag/m$^2$, gelatin at 3.77 gm/m$^2$, and one of the couplers designated in Table II dispersed in half its weight of tricresyl phosphate and coated at 1.62 mmol/m$^2$. The photosensitive layer was overcoated with a layer containing gelatin at 1.08 gm/m$^2$ and bis-vinylsulfonylmethyl ether at 1.75 weight percent based on total gelatin.

Samples of each element were imagewise exposed through a graduated-density test object and processed at 40° C. employing the following color developing solution, then stopped, bleached, fixed, washed, and dried to produce stepped magenta dye images.

| | |
|---|---|
| K$_2$SO$_3$ | 2.0 gm |
| K$_2$CO$_3$ | 30.0 gm |
| KBr | 1.25 gm |
| KI | 0.6 gm |
| 4-Amino-3-methyl-N-ethyl-N—B'-hydroxyethylaniline sulfate | 3.55 gm |
| Water to 1.0 liter, pH 10.0 | |

Densitometry of these images provided measures of maximum density (D$_{max}$). Dye hues were obtained from spectrophotometric curves by measuring the maximum absorption peak (λmax) normalized to 1.0 density.

Described Compound No. III was used as the magenta dye-forming coupler of Example 1. Described Compound II was used as the magenta dye-forming coupler of Example 2. The results are given in the following Tables.

TABLE II

| Example No. | Compound No. | λ max | Dmax | Dmin |
|---|---|---|---|---|
| 1 | III | 560 | 3.94 | .21 |
| 2 | II | 567 | 3.98 | .14 |
| Comparison A | *C-8 | 555 | 3.03 | .13 |

TABLE III

| Example No. | Compound No. | λ max | Dmax | Dmin |
|---|---|---|---|---|
| 3 | V | 562 | 3.93 | .15 |
| Comparison A | *C-8 | 556 | 3.62 | .14 |

TABLE IV

| Example No. | Compound No. | λmax | Dmax | Dmin |
|---|---|---|---|---|
| 4 | VI | 561 | 4.05 | .13 |
| 5 | VII | 563 | 3.87 | .12 |
| Comparison A | *C-8 | 556 | 3.32 | .14 |

*Structure of comparison coupler C-8:
C-8

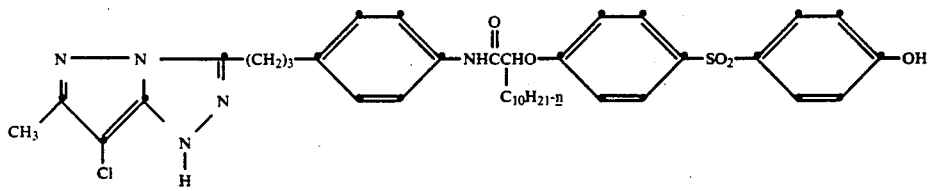

This data demonstrates the shift in hue and increased maximum density provided by the couplers of the invention compared to Comparison A (Compound C-8). The photographic elements of Examples 1 and 2 also provide higher contrast and higher relative speed compared to a photographic element containing comparison coupler A.

Other examples of useful pyrazoloazole couplers are as follows: these can be prepared by methods like those described above and can be used in a color photographic element as described in Example 1.

TABLE V

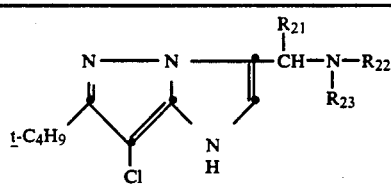

| Example No. | R$_{21}$ | R$_{22}$ | R$_{23}$ |
|---|---|---|---|
| 6 | —C$_2$H$_5$ | H | (structure shown below) |

—NHCCHO—⟨benzene⟩—SO$_2$—⟨benzene⟩—OH with C$_{10}$H$_{21}$-n

TABLE V-continued
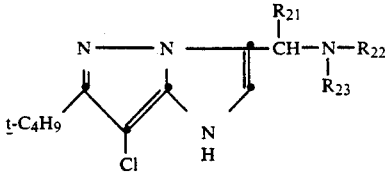
| Example No. | $R_{21}$ | $R_{22}$ | $R_{23}$ |
|---|---|---|---|
| 7 | $-C_2H_5$ | $CH_3$ | 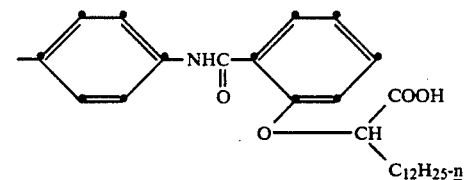 |
| 8 | $-C_{10}H_{21}\text{-}\underline{n}$ | H | 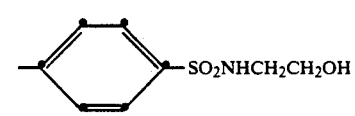 |
| 9 | $-C_{12}H_{25}\text{-}\underline{n}$ | H | 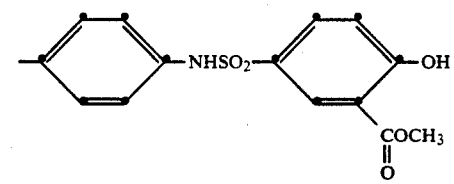 |
| 10 | $-C_{12}H_{25}\text{-}\underline{n}$ | $C_{12}H_{25}\text{-}\underline{n}$ | 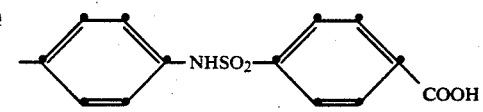 |
| 11 | $-C_{12}H_{25}\text{-}\underline{n}$ | $CH_3$ | 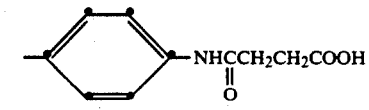 |
| 12 | $-C_{18}H_{37}\text{-}\underline{n}$ | H | 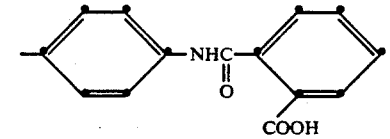 |
TABLE VI
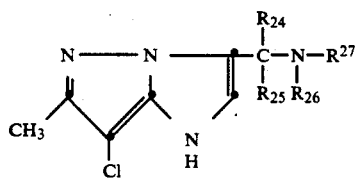
| Example No. | $R_{24}$ | $R_{25}$ | $R_{26}$ | $R_{27}$ |
|---|---|---|---|---|
| 13 | 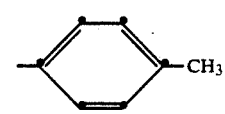 | H | $CH_3$ | 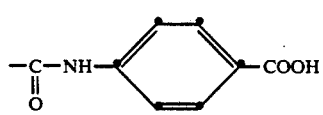 |

TABLE VI-continued

Structure: pyrazole ring with CH₃, Cl substituents, linked to C(R₂₄)(R₂₅)–N(R₂₆)(R₂⁷), with NH group.

| Example No. | R₂₄ | R₂₅ | R₂₆ | R₂₇ |
|---|---|---|---|---|
| 14 | —C₁₀H₂₁-n | —C₂H₅ | C₂H₅ | —CH₂—C₆H₃(OCH₃)—NHSO₂—C₆H₄—COOH |
| 15 | —CH₂—C₆H₅ | H | C₂H₅ | —CH₂—naphthyl—COOH |
| 16 | —C₂H₅ | —C₂H₅ | C₂H₅ | C₅H₁₀COOH |
| 17 | —C₂H₅ | H | —C₂H₅ | C₁₈H₃₆COOH |
| 18 | —C₂₀H₄₁-n | H | H | CH₂CH₂COOH |
| 19 | —C₁₂H₂₅-n | H | —C₄H₉-n | —C(=O)CH₂CH₂COOH |
| 20 | C₂H₅ | C₂H₅ | C₁₈H₃₇-n | —C(=O)CH₂COOH |
| 21 | C₁₀H₂₁-n | H | H | —CH₂—C₆H₄—NHSO₂—C₆H₄—COOH |
| 22 | C₂H₅ | H | H | —CH₂—C₆H₃—NHC(=O)—C₆H₃(O—CH(C₁₂H₂₅-n)—COOH) |

TABLE VI-continued

[Structure shown at top of table: pyrazole ring with CH₃, Cl substituents, connected to C(R24)(NH)=... with C(R25)(R26)-N(R27) group]

| Example No. | $R_{24}$ | $R_{25}$ | $R_{26}$ | $R_{27}$ |
|---|---|---|---|---|
| 23 | $C_{12}H_{25}\text{-}\underline{n}$ | $CH_3$ | $C_{18}H_{37}\text{-}\underline{n}$ | —C(=O)NH—C₆H₄—COOH |
| 24 | $C_2H_5$ | H | $C_{18}H_{37}\text{-}\underline{n}$ | —C(=O)NH—C₆H₄—COOH |
| 25 | $C_2H_5$ | H | $CH_3$ | —C(=O)NH—C₆H₄—COOH |
| 26 | $C_{12}H_{25}\text{-}\underline{n}$ | H | $C_4H_9\text{-}\underline{i}$ | —C(=O)CH₂CH₂COOH |
| 27 | $C_2H_5$ | H | —C(=O)CH₂CH₂COOH | —(CH₂)₄—O—C₆H₃(C₅H₁₁-t)(C₅H₁₁-t) |
| 28 | $C_{12}H_{25}\text{-}\underline{n}$ | H | $C_8H_{17}\text{-}\underline{n}$ | —C(=O)CH₂CH₂COOH |
| 29 | $C_2H_5$ | H | $C_8H_{17}\text{-}\underline{n}$ | $C_8H_{17}\text{-}\underline{n}$ |
| 30 | $C_{12}H_{25}\text{-}\underline{n}$ | H | $CH_3$ | —C₆H₅ |
| 31 | $C_{12}H_{25}\text{-}\underline{n}$ | H | $CH_3$ | —C₆H₄—OCH₃ |
| 32 | $C_2H_5$ | H | $C_{12}H_{25}\text{-}\underline{n}$ | —C₆H₄—OH |
| 33 | $C_{12}H_{25}\text{-}\underline{n}$ | H | $C_2H_4OC_2H_4OC_2H_4OCH_3$ | $C_2H_4OC_2H_4OC_2H_4OCH_3$ |
| 34 | $C_2H_5$ | H | $CH_3$ | —C₆H₄—CO₂CH₃ |
| 35 | $C_{12}H_{25}\text{-}\underline{n}$ | H | $C_2H_4OH$ | $C_2H_4OH$ |
| 36 | $C_{12}H_{25}\text{-}\underline{n}$ | H | morpholino (N,O 6-ring) | |

TABLE VI-continued $$\begin{array}{c} \text{structure with } R_{24}, R_{25}, R_{26}, R_{27}, CH_3, Cl, NH \end{array}$$

| Example No. | $R_{24}$ | $R_{25}$ | $R_{26}$ | $R_{27}$ |
|---|---|---|---|---|
| 37 | $C_{12}H_{25}\text{-}n$ | H | $CH_3$ | $CH_2CH_2CO_2C_2H_5$ |

The compounds of the invention of these examples also enable reduced silver interaction.

The invention has been described in detail with particular reference to preferred embodiments thereof, but it will be understood that variations and modifications can be effected within the spirit and scope of the invention.

What is claimed is:

1. A photographic element comprising a support, at least one photographic silver halide emulsion and a photographic pyrazoloazole coupler having substituted on the azole ring of the coupler a group represented by the structure:

$$\begin{array}{c} R_1 \\ | \\ -C-N-R_4 \\ | \ \ | \\ R_2 \ R_3 \end{array}$$

wherein:

$R_1$ and $R_2$ are individually hydrogen, unsubstituted or substituted alkyl or unsubstituted or substituted aryl;

$R_3$ and $R_4$ are individually hydrogen, unsubstituted or substituted alkyl, unsubstituted or substituted aryl, or $$\begin{array}{c} O \\ \| \\ C-R_5; \end{array}$$

wherein at least one of $R_3$ and $R_4$ is alkyl, aryl or $$\begin{array}{c} O \\ \| \\ C-R_5; \end{array}$$

$R_5$ is unsubstituted or substituted alkyl, unsubstituted or substituted aryl, or $NH-R_6$; and $R_6$ is unsubstituted or substituted alkyl or unsubstituted or substituted aryl and wherein the photographic silver halide emulsion is a silver bromoiodide emulsion.

2. A photographic element as in claim 1 wherein the pyrazoloazole coupler is a pyrazolotriazole coupler.

3. A photographic element as in claim 1 wherein the pyrazoloazole coupler comprises at least one water solubilizing group.

4. A photographic element as in claim 1 comprising a red-sensitive silver halide emulsion unit having associated therewith a cyan dye image forming material, a green-sensitive silver halide emulsion unit having associated therewith a magenta dye image forming material, and a blue-sensitive silver halide emulsion unit having associated therewith a yellow dye-image forming material, and wherein said pyrazoloazole coupler is associated with at least one of said units.

5. A photographic element as in claim 1 wherein at least one $R_1$ and $R_2$ is alkyl or aryl.

6. A photographic element comprising a support, at least one photographic silver halide emulsion and a photographic coupler represented by the structure:

$$\begin{array}{c} \text{structure with } J, Q, X, Y, Z, R_8, R_9, R_{10}, R_{11} \end{array}$$

wherein:

J is a substituent;

Q is hydrogen or a coupling-off group;

X, Y and Z are individually selected from carbon and nitrogen atoms necessary to complete an azole ring;

$R_8$ and $R_9$ are individually hydrogen, unsubstituted or substituted alkyl or unsubstituted or substituted aryl;

$R_{10}$ and $R_{11}$ are individually hydrogen, unsubstituted or substituted alkyl, unsubstituted or substituted aryl or $$\begin{array}{c} O \\ \| \\ C-R_{12}; \end{array}$$

wherein at least one of $R_{10}$ and $R_{11}$ is alkyl, aryl or $$\begin{array}{c} O \\ \| \\ C-R_{12}; \end{array}$$

$R_{12}$ is unsubstituted or substituted alkyl, unsubstituted or substituted aryl or $NH-R_{13}$;

$R_{13}$ is unsubstituted or substituted alkyl or unsubstituted or substituted aryl and further wherein said silver halide emulsion is a silver bromoiodide emulsion.

7. A photographic element as in claim 6 wherein the pyrazoloazole coupler is a 1H-pyrazolo [3,2-c]-s-triazole represented by the structure:

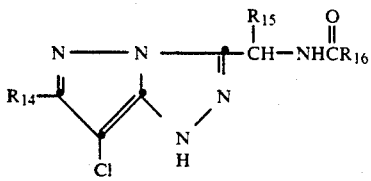

wherein:
- $R_{14}$ is a substitutent;
- $R_{15}$ is unsubstituted or substituted alkyl;
- $R_{16}$ is unsubstituted or substituted alkyl, or $NH-R_{17}$;
- $R_{17}$ is unsubstituted or substituted alkyl or unsubstituted or substituted aryl; and
- Q is hydrogen or a coupling-off group.

8. A photographic element as in claim 6 wherein the pyrazoloazole coupler is a compound selected from the group consisting of:

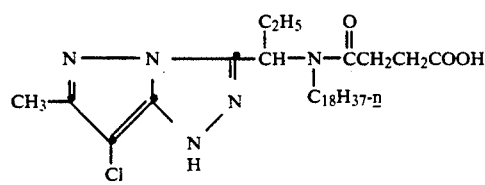

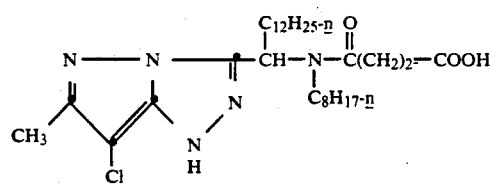

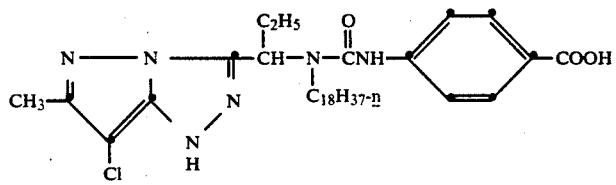

and

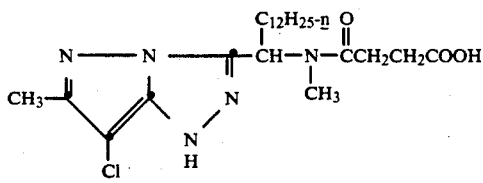

9. A process of forming a photographic image which comprises developing an exposed silver halide emulsion layer with a color developing agent in the presence of a photographic pyrazoloazole coupler wherein the pyrazoloazole coupler has substituted on the azole ring of the coupler a group represented by the formula:

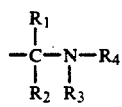

wherein:

$R_1$ and $R_2$ are individually hydrogen, unsubstituted or substituted alkyl, or unsubstituted or substituted aryl;

$R_3$ and $R_4$ are individually hydrogen, unsubstituted or substituted alkyl, unsubstituted or substituted aryl, or

wherein at least one of $R_3$ and $R_4$ is alkyl or aryl or

$R_5$ is unsubstituted or substituted alkyl, or $NH-R_6$; and

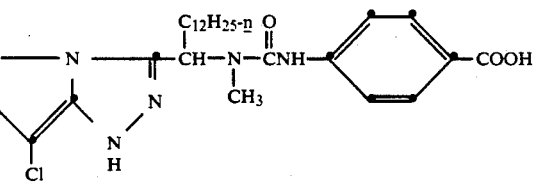

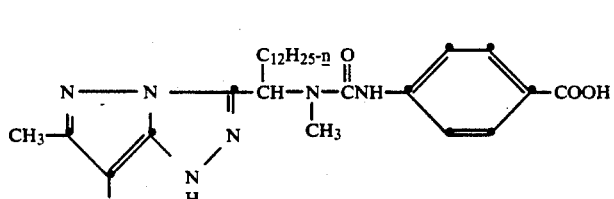

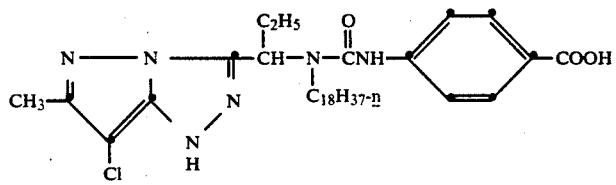

$R_6$ is unsubstituted or substituted alkyl, or unsubstituted or substituted aryl and further wherein said silver halide emulsion layer is a silver bromoiodide emulsion layer.

10. A process as in claim 9 wherein the pyrazoloazole coupler is a pyrazolotriazole.

11. A process as in claim 9 wherein the pyrazoloazole coupler is a 1H-pyrazolo[3,2-c]-s-triazole represented by the structure:

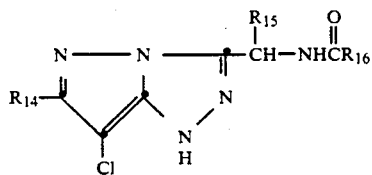

wherein:
$R_{14}$ is a substituent;
$R_{15}$ is unsubstituted or substituted alkyl;
$R_{16}$ is unsubstituted or substituted alkyl or $NH-R_{17}$;
$R_{17}$ is unsubstituted or substituted alkyl or unsubstituted or substituted aryl; and
Q is hydrogen or a coupling-off group.

12. A process as in claim 9 wherein the pyrazoloazole coupler is a compound selected from the group consisting of

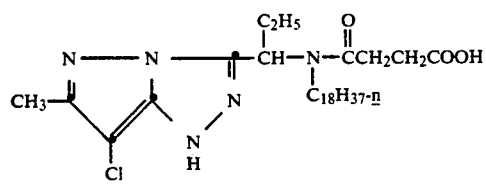
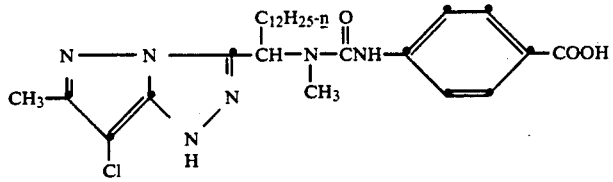
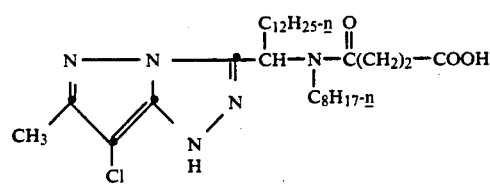
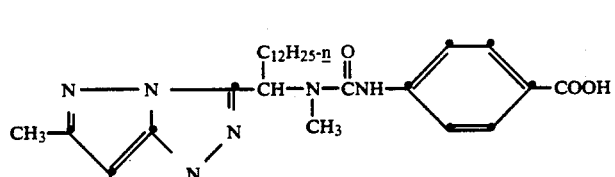
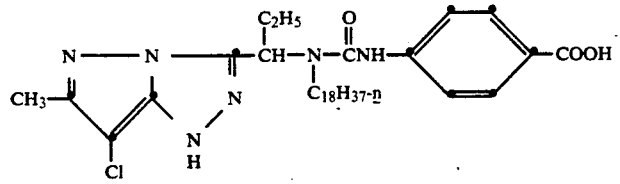

and

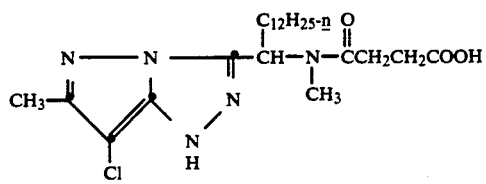

13. A process as in claim 9 wherein at least one of $R_1$ and $R_2$ are alkyl or aryl.

14. A photographic element comprising a support, at least one silver halide emulsion and a photographic pyrazolotriazole coupler having substituted on the azole ring of the coupler a group containing a carbon atom (A) bonded directly to the azole ring and wherein the carbon atom (A) is bonded directly to a nitrogen atom in the group and to an unsubstituted or substituted alkyl or aryl group and further wherein said emulsion is a photographic silver bromoiodide emulsion.

15. A photographic element comprising a support, at least one silver halide emulsion and a pyrazolo[3,2-c]-s-triazole coupler having in the 3-position a ballast group containing a carbon atom (A) bonded directly to the pyrazolo[3,2-c]-s-triazole nucleus and wherein the carbon atom (A) is bonded directly to a nitrogen atom in the ballast group and to an unsubstituted or substituted alkyl or aryl group and further wherein said emulsion is a photographic silver bromoiodide emulsion.

16. A photographic element as in claim 15 wherein the element comprises a support bearing at least one red-sensitive silver halide emulsion layer comprising a cyan image dye-forming coupler; at least one green-sensitive silver halide emulsion layer comprising a magenta image dye-forming coupler; and at least one blue-sensitive silver halide emulsion layer comprising a yellow image dye-forming coupler and wherein the pyrazolo[3,2-c]-s-triazole is represented by the formula:

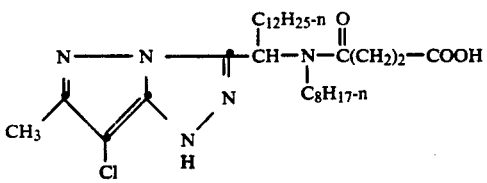

17. A photographic element as in claim 15 wherein the coupler comprises at least one water solubilizing group on the ballast group.

* * * * *

UNITED STATES PATENT AND TRADEMARK OFFICE
CERTIFICATE OF CORRECTION

PATENT NO. : 5,183,728
DATED : February 2, 1993
INVENTOR(S) : R. F. Romanet et al It is certified that error appears in the above-indentified patent and that said Letters Patent is hereby corrected as shown below:

In Column 41, first strucutre, delete "Cl" and insert --Q--.
In Column 43, first strucutre, delete "Cl" and insert --Q--.

Signed and Sealed this

Seventh Day of February, 1995

Attest:

BRUCE LEHMAN

*Attesting Officer*          *Commissioner of Patents and Trademarks*